US008926986B2

(12) United States Patent
Kubler-Kielb et al.

(10) Patent No.: US 8,926,986 B2
(45) Date of Patent: Jan. 6, 2015

(54) USE OF SACCHARIDES CROSS-REACTIVE WITH *BACILLUS ANTHRACIS* SPORE GLYCOPROTEIN AS A VACCINE AGAINST ANTHRAX

(71) Applicants: The United States of America as Represented by the Secretary of the Department of Health and Human Services, Bethesda, MD (US); National Research Council of Canada, Ottawa (CA)

(72) Inventors: Joanna Kubler-Kielb, Bethesda, MD (US); Evguenii Vinogradov, Ottawa (CA); Rachel Schneerson, Bethesda, MD (US); Haijing Hu, Montgomery Village, MD (US); Stephen H. Leppla, Bethesda, MD (US); John B. Robbins, New York, NY (US)

(73) Assignees: National Research Council of Canada, Ottawa, ON (CA); The United States of America, as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 13/909,992

(22) Filed: Jun. 4, 2013

(65) Prior Publication Data
US 2013/0273097 A1 Oct. 17, 2013

Related U.S. Application Data

(62) Division of application No. 12/918,281, filed as application No. PCT/US2009/000995 on Feb. 17, 2009.

(60) Provisional application No. 61/066,509, filed on Feb. 19, 2008.

(51) Int. Cl.
*A61K 39/385* (2006.01)
*A61K 47/48* (2006.01)
*C07H 3/06* (2006.01)
*A61K 39/02* (2006.01)
*A61K 39/104* (2006.01)
*A61K 39/00* (2006.01)

(52) U.S. Cl.
CPC ............ *C07H 3/06* (2013.01); *A61K 47/48284* (2013.01); *A61K 47/4833* (2013.01); *A61K 203/6081* (2013.01); *A61K 2039/521* (2013.01); *A61K 39/0208* (2013.01); *A61K 39/00* (2013.01); *A61K 39/104* (2013.01)
USPC .................................................. 424/197.11

(58) Field of Classification Search
None
See application file for complete search history.

(56) References Cited

U.S. PATENT DOCUMENTS 6,248,329 B1 * 6/2001 Chandrashekar et al. . 424/191.1
2005/0118194 A1   6/2005 Sin et al.
2007/0141084 A1   6/2007 Lee et al.

OTHER PUBLICATIONS

Feng et al (Infection and Immunity, 64(1):363-365, 1996).*
Hecht et al. (Current Opinion in Chemical Biology, 13:354-359, 2009.*
Enkhtuya et al (Microbiology, 152:3103-3110, 2006).*
Waller et al, Journal of Bacteriology, 187(13:4592-4597, 2005.*
Wang et al Proteomics, 7:180-184, 2007.*
Oberli et al, Organic Letters, 10(5):905-908, 2008.*
Campbell, Monoclonal Antibody Technology, Elsevier Science Publishers B.V., Chapter 2, 1984.
Daubenspeck et al., "Novel Oligosaccharide Side Chains of the Collagen-like Region of Bc1A, the Major Glycoprotein of the *Bacillus anthracis* Exosporium," *Journal of Biological Chemistry* 279(30):30945-30953, 2004.
Kubler-Kielb et al., "Saccharides cross-reactive with *Bacillus anthracis* spore glycoprotein as an anthrax vaccine component," *Proceedings of the National Academy of Sciences of the United States of America* 105(25):8709-8712, Jun. 2008.
Mehta et al., "Synthesis and antigenic analysis of the Bc1A glycoprotein oligosaccharide from the *Bacillus anthracis* exosporium," *Chemistry—A European Journal* 12(36):9136-9149, Dec. 2006.
Takeuchi et al., "Flagellin Glycans from two pathovars of Pseudomonas syringae contain rhamnose in D and L configurations in different rations and modified 4-amino-4, 6-dideoxyglucose," *Journal of Bacteriology* 189(19):6945-6956, Oct. 2007.
Venkateswaran et al., "Polyphasic taxonomy of the genus *Shewanella* and description of *Shewanella oneidensis* sp. nov.," *International Journal of Systematic Bacteriology* 49:705-724, 1999.
Vinogradov et al., "The structure of the capsular polysaccharide of *Shewanella oneidensis* strain MR-4," *Carbohydrate Research* 340(10):1750-1753, Jul. 2005.
Wang et al., "Photogenerated glycan arrays identify immunogenic sugar moieties of *Bacillus anthracis* exosporium," *Proteomics* 7:180-184, 2007.
International Search Report from PCT Application No. PCT/US2009/000995, dated Aug. 27, 2009.
Written Opinion of the International Searching Authority from PCT Application No. PCT/US2009/000995, dated Aug. 27, 2009.

* cited by examiner

*Primary Examiner* — Patricia A Duffy
(74) *Attorney, Agent, or Firm* — Klarquist Sparkman, LLP

(57) ABSTRACT

Provided are immunogenic compositions and methods for eliciting an immune response against *B. anthracis* and other bacteria that contain 3-methyl-3-hydroxybutyrate- or 3-hydroxybutyrate-substituted saccharides. Conjugates of 3-methyl-3-hydroxybutyrate- or 3-hydroxybutyrate-substituted saccharides elicit an effective immune response against *B. anthracis* spores in mammalian hosts to which the conjugates are administered.

4 Claims, 3 Drawing Sheets

S-anti-spore serum
1-CPS$_{TSB}$ 0.5 mg/ml, 2-CPS$_{TSB}$ 0.2 mg/ml
2-CPS$_{CDM}$ 0.5 mg/ml, 2-CPS$_{CDM}$ 0.2 mg/m

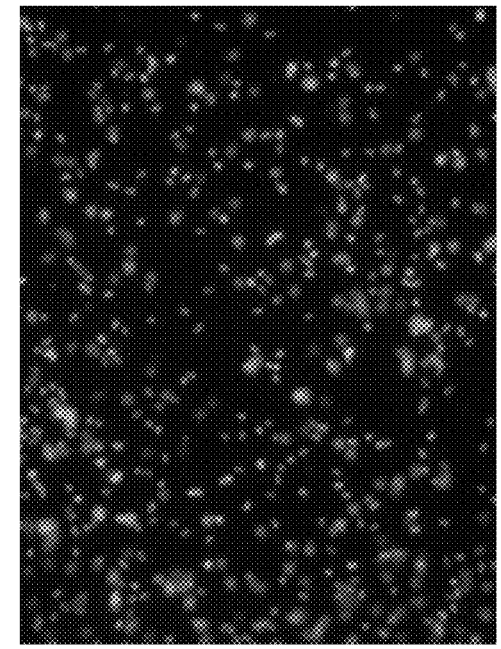
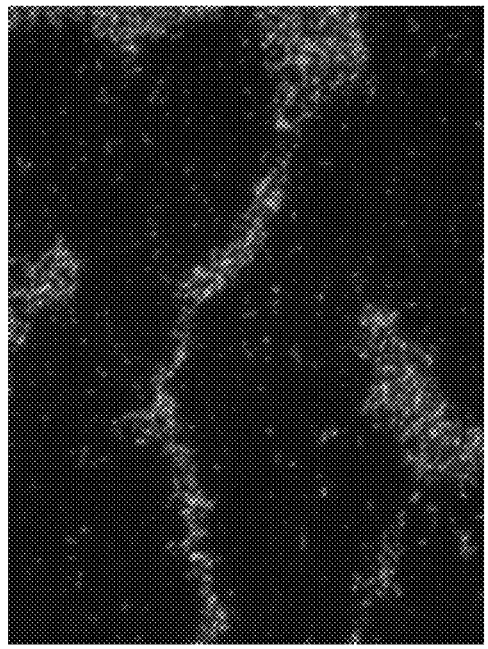
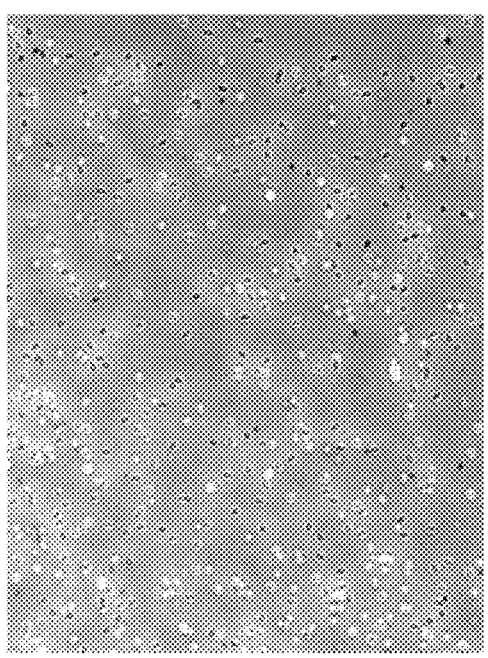
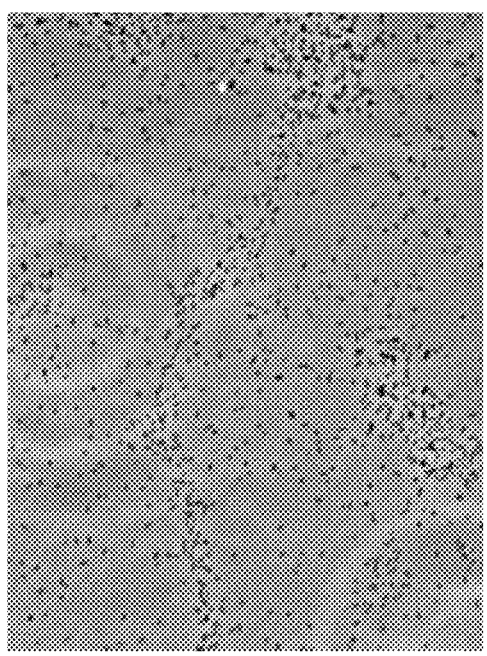
FIG. 3A
FIG. 3B

USE OF SACCHARIDES CROSS-REACTIVE WITH *BACILLUS ANTHRACIS* SPORE GLYCOPROTEIN AS A VACCINE AGAINST ANTHRAX

This is a divisional application of U.S. application Ser. No. 12/918,281, filed on Aug. 18, 2010, which is the U.S. National Stage of International Application No. PCT/US2009/000995, filed Feb. 17, 2009, published in English under PCT Article 21(2) which claims the benefit of U.S. Provisional Application No. 61/066,509, filed Feb. 19, 2008, which are incorporated herein by reference in their entirety.

FIELD

The disclosure relates to identifying compounds useful for generating vaccines against anthrax. Methods of generating and using the compounds, along with the vaccines developed from the compounds are also disclosed.

BACKGROUND

Anthrax is a potentially lethal human infection. The causative organism is a Gram-positive rod-shaped bacterium, *Bacillus anthracis*, which exists in a vegetative or a spore form. Spores are the infecting agent; infection is initiated by entry of spores into a mammalian host. Entry can be by intradermal inoculation, ingestion, or inhalation. The most lethal form of anthrax in humans is pulmonary infection caused by inhalation of *B. anthracis* spores.

Like all *Bacillus* species, *B. anthracis* bacteria form spores when subjected to adverse conditions. Mature spores are dormant and highly resistant to heat, dryness, and aggressive chemical conditions. They can survive in soil for decades.

Upon entry into a suitable host, the spores germinate and multiply rapidly. The bacteria then release the anthrax toxins toxic to the host.

Most *Bacillus* spores consist of a central genome-containing core surrounded by two protective layers: the cortex and the coat. The outer layer of most *Bacillus* spores is the spore coat comprised of different proteins. Mature spores of *Bacillus* species such as *B. anthracis* contain an additional loose-fitting layer called an exosporium. The exosporium is the outermost layer for *B. anthracis* and interacts with the environment/host. The exosporium is the primary permeability barrier of the spore and contains spore surface antigens.

Analysis of the exosporium identified several protein including a glycoprotein called BclA (*Bacillus* collagen-like protein of *anthracis*). BclA is a structural component and contains multiple collagen-like Xaa-Yaa-Gly repeats. BclA is an immuno-dominant protein on the *B. anthracis* spore surface because most of the antibodies raised against spores react with this protein.

An unusual tetrasaccharide is attached to the BclA protein, likely through a GalNAc linkage. This tetrasaccharide consists of three rhamnose monosaccharides linked to a sugar residue called anthrose [2-O-methyl-4-(3-hydroxy-3-methylbutanamido)-4,6-dideoxy-β-D-glucose]. Anthrose was reported to be unique to *B. anthracis* spores, however the anthrose biosynthesis genes were recently identified also in other bacilli and it was demonstrated that anthrose expression is not restricted to *B. anthracis*.

SUMMARY

In one aspect, different components of *Shewanella* spp. MR-4 or *Pseudomonas syringae* are used to develop anthrax vaccines. For example, capsular polysaccharides from *Shewanella* spp. MR-4 (and similar saccharides as described below) are used to generate an immune response in a subject and to develop anthrax vaccines. In another example, compounds from the flagella of *Pseudomonas syringae* are used to generate an immune response in a subject and to develop anthrax vaccines.

In one embodiment, there is disclosed a pharmaceutical composition comprising at least one immunogenic agent that is cross-reactive with *B. anthracis*, wherein the immunogenic agent is selected from:

(a) at least one compound comprising:

-4)-β-D-Man-(1-4)-β-D-Glc-1-3-β-D-GlcNAc-(1-,
|
4)-α-D-GlcA-(1-3)

-4)-β-D-Man-(1-4)-β-D-Glc-1-3-β-D-GlcNAc-(1-
|
4)-α-D-GlcA-(1-3)     or

3)-α-L-Rhap-(1-2)-α-L-Rha-(1-O-Ser (b) an isolated *B. anthracis* antigenic component from *Shewanella* or *P. syringae*;

(c) killed whole cells of *Shewanella* or *P. syringae*; or (d) any combination or mixture of (a)-(c).

In another embodiment, there is disclosed a pharmaceutical composition comprising at least one compound that is cross-reactive with *B. anthracis*, wherein the compound comprises

[Structure: H3C-C(CH3)(OH)-CH2-C(=O)-NH-sugar with H3C, HO, OH substituents] -4)-β-D-Man-(1-4)-β-D-Glc-1-3-β-D-GlcNAc-(1-,
                                                                                                                   |
                                                                                                              -4)-α-D-GlcA-(1-3)

[Structure: H3C-CH(OH)-CH2-C(=O)-NH-sugar (with stereochemistry H, OH)] -4)-β-D-Man-(1-4)-β-D-Glc-1-3-β-D-GlcNAc-(1-  or
                                                                                                                   |
                                                                                                              -4)-α-D-GlcA-(1-3)

[Structure: H3C-C(CH3)(OH)-CH2-C(=O)-NH-sugar with OCH3] 3)-α-L-Rhap-(1-2)-α-L-Rha-(1-O-Ser and at least one pharmaceutically acceptable additive.

In another embodiment, there is disclosed an antibody that is immuno-reactive to a compound comprising

[Structure] -4)-β-D-Man-(1-4)-β-D-Glc-1-3-β-D-GlcNAc-(1-,
                                                    |
                                               -4)-α-D-GlcA-(1-3)

[Structure] -4)-β-D-Man-(1-4)-β-D-Glc-1-3-β-D-GlcNAc-(1-  or
                                                    |
                                               -4)-α-D-GlcA-(1-3)

[Structure] 3)-α-L-Rhap-(1-2)-α-L-Rha-(1-O-Ser wherein the antibody is also immuno-reactive to *B. anthracis* spores.

According to a further embodiment, there is disclosed a vaccine comprising at least one immunogenic agent that is cross-reactive with *B. anthracis*, wherein the immunogenic agent is selected from:

(a) at least one compound comprising:

[Structure] -4)-β-D-Man-(1-4)-β-D-Glc-1-3-β-D-GlcNAc-(1-,
                                                    |
                                                4)-α-D-GlcA-(1-3)

[Structure] -4)-β-D-Man-(1-4)-β-D-Glc-1-3-β-D-GlcNAc-(1-
                                                    |
                                                4)-α-D-GlcA-(1-3)                                              or

[Structure] 3)-α-L-Rhap-(1-2)-α-L-Rha-(1-O-Ser (b) an isolated *B. anthracis* antigenic component from *Shewanella* or *P. syringae;*
(c) killed whole cells of *Shewanella* or *P. syringae;* or
(d) any combination or mixture of (a)-(c).

Another disclosed embodiment is an immunogenic conjugate comprising at least one moiety selected from covalently linked to a carrier, wherein the conjugate elicits an immune response in a subject.

There are also disclosed methods for inhibiting a *Bacillus* infection in a subject, or stimulating an immune response in a subject against *B. anthracis*, that comprise administering the pharmaceutical compositions or immunogenic conjugates disclosed herein.

Another aspect relates to a compound of general formula in which
$R_1$ is selected from the group consisting of —H, —OH, —CH$_3$, C$_2$ to C$_6$ alkyl, and C$_2$ to C$_6$ alkoxy;
$R_2$ is selected from the group consisting of —H, —OH, —CH$_3$, C$_2$ to C$_6$ alkyl, and C$_2$ to C$_6$ alkoxy;
$R_3$ is selected from the group consisting of —H, —OH, —CH$_3$, C$_2$ to C$_6$ alkyl, and C$_2$ to C$_6$ alkoxy;
$R_4$ is selected from the group consisting of —H, —OH, —CH$_3$, C$_2$ to C$_6$ alkyl, and C$_2$ to C$_6$ alkoxy;
$R_5$ is selected from the group consisting of —H, —OH, —CH$_3$, C$_2$ to C$_6$ alkyl, and C$_2$ to C$_6$ alkoxy; and
$R_6$ is selected from the group consisting of —H, —OH, —CH$_3$, C$_2$ to C$_6$ alkyl, C$_2$ to C$_6$ alkoxy, and (—OR$_7$)$_n$, wherein R$_7$ is a sugar molecule and n is 0 to 20.

The sugars can be straight-chain, furanose, or pyranose; D- or L-; α- or β-linked; and linked from any position on the ring of one sugar to any position on the ring of another sugar. The compound of general formula is not any of:

-continued
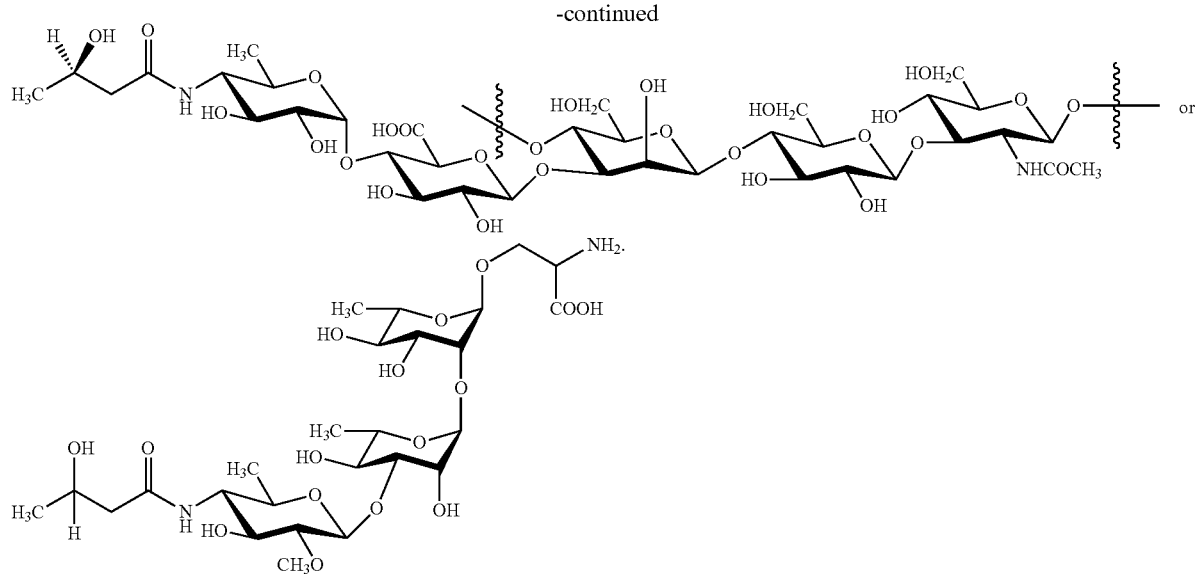
Another aspect relates to a pharmaceutical composition comprising the compound of general formula
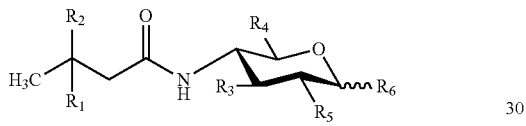
and a pharmaceutically acceptable carrier, where the compound of general formula is not:
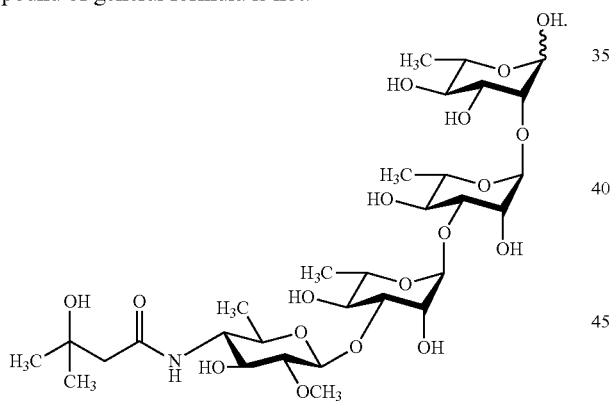
In another aspect the compound of general formula
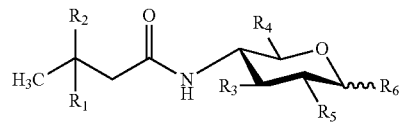
is covalently attached to a polypeptide, where the compound of general formula is not any of:
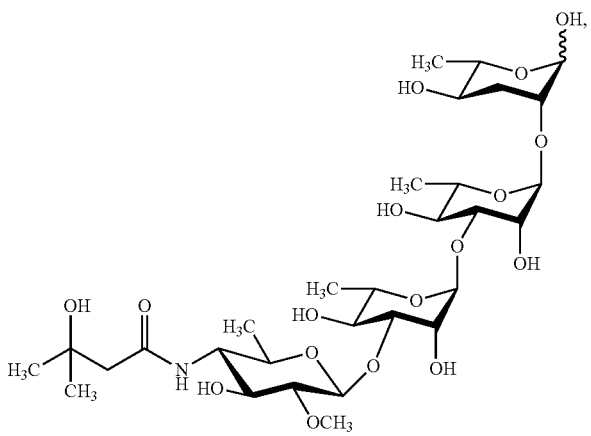

[Chemical structures shown]

In another aspect the compound of general formula

[Chemical structure shown]

is attached to an immunogenic conjugate.

Another aspect relates to antibodies raised against the compound of general formula

[Chemical structure shown]

In another aspect, the compound of general formula

[Chemical structure shown]

is used to generate an immune response in a subject. Preferably an immune response is generated against *B. anthracis* spores.

In another aspect, the compound of general formula

[Chemical structure shown]

is used to test the selectivity of *B. anthracis* antibodies.

Another aspect relates to the use of capsular polysaccharides from *Shewanella* and compounds from the flagella of *Pseudomonas syringae* as substitutes for BclA tetrasaccharide and glycoprotein in the development of anthrax vaccines. Alternatively, the capsular polysaccharide is part of a glycoprotein, such as a *Shewanella* MR-4 or *P. syringae* glycoprotein, or the polysaccharide is conjugated to another carrier protein such as bovine serum albumin.

BRIEF DESCRIPTION OF THE FIGURES

FIG. 3A to 3B show immunofluorescent staining of *B. anthracis* spores and *P. syringae* cells treated with anti-spore serum.

DETAILED DESCRIPTION

Abbreviations

Figure 1:
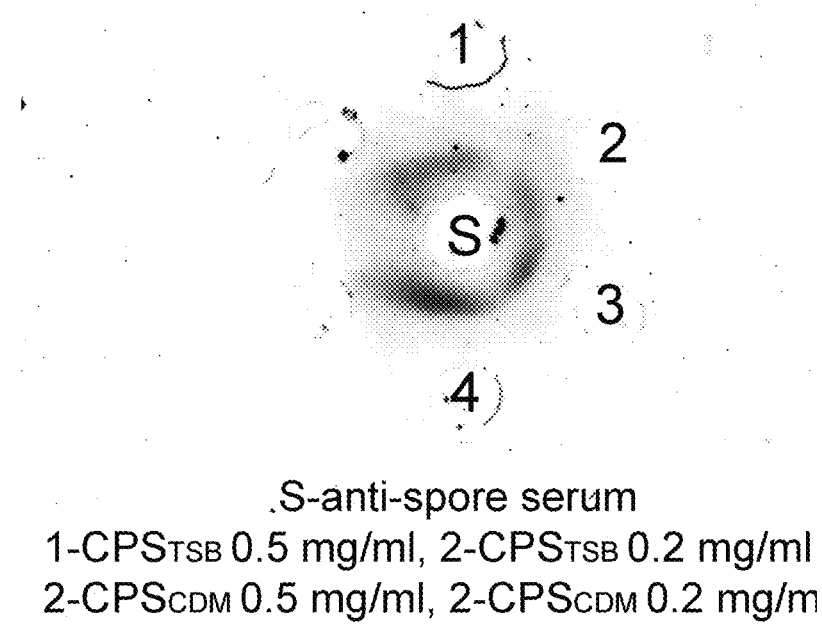
FIG. 1 shows immunodiffusion of two *Shewanella* spp. MR-4 capsular polysaccharides against serum to *B. anthracis* spore spores.
Figure 2A:
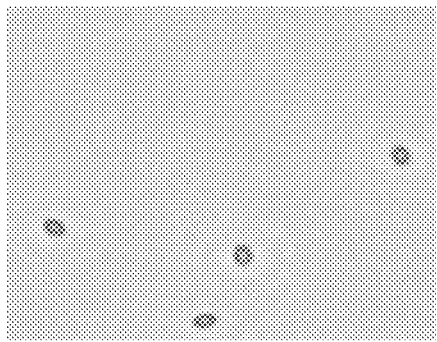
FIG. 2A to 2D show immunofluorescent staining of *B. anthracis* spores treated with four antibodies.
Figure 2A:
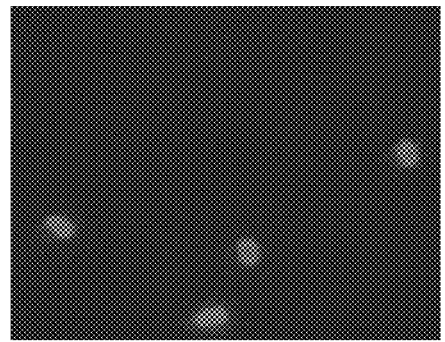
Figure 2B:
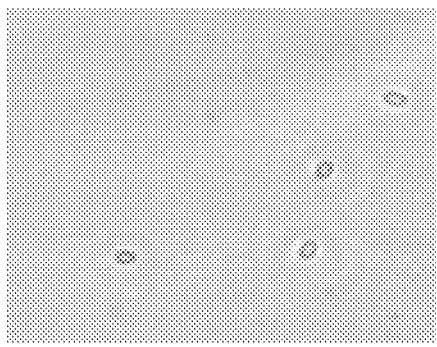
Figure 2B:
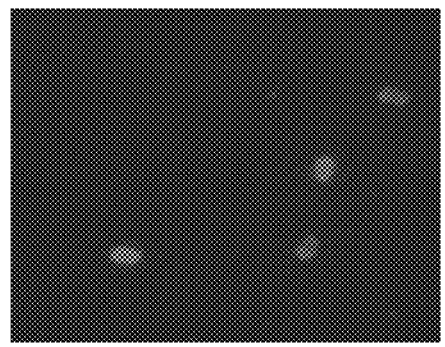
Figure 2C:
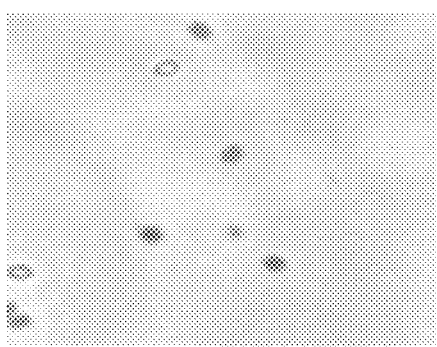
Figure 2C:
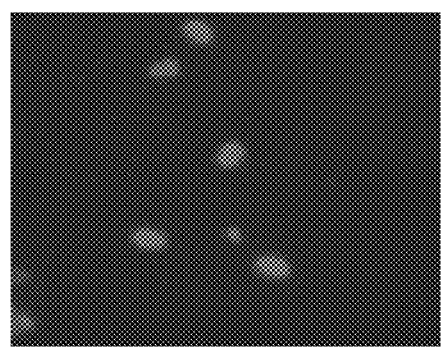
Figure 2D:
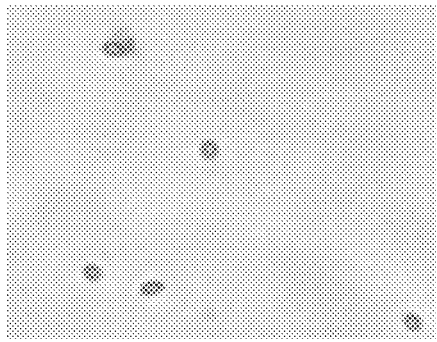
Figure 2D:
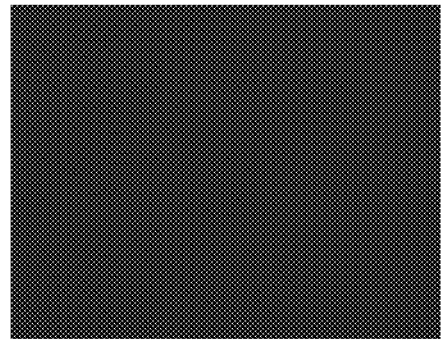

BclA is *Bacillus* collagen-like protein of anthracis.
ELISA is enzyme-linked immuno-absorbent assay.

HMB is 3-hydroxy-3-methylbutyrate.
HB is 3-hydroxy-butyrate.

Terms and Definitions

An "adjuvant" is a substance that helps and enhances the pharmacological effect of a drug or increases the ability of an antigen to stimulate the immune system. Adjuvants can be used to improve the immune response to vaccine antigens for several different purposes, including: (1) increasing the immunogenicity of weak antigens; (2) enhancing the speed and duration of the immune response; (3) modulating antibody avidity, specificity, isotype or subclass distribution; (4) stimulating cell mediated immunity; (5) promoting the induction of mucosal immunity; (6) enhancing immune responses in immunologically immature or senescent individuals; (7) decreasing the dose of antigen in the vaccine to reduce costs or (8) helping to overcome antigen competition in combination vaccines. Examples of adjuvants include Freund's complete adjuvant, Freund's incomplete adjuvant, saponin, aluminum hydroxide (for example, Amphogel, WYETH Laboratories, Madison, N.J.), MF59, MTP-PE, QA-21, ISA51, B30-MDP, LA-15-PH, MPL (3-O-deacylated monophosphoryl lipid A; Corixa, Hamilton Ind.), 3D-MPL, oil emulsions, lipopolysaccharides, polymers, liposomes, cytokines, IL-12 (Genetics Institute, Cambridge Mass.), ISCOMs, or other available adjuvants or adjuvant combinations. A general discussion of vehicles and adjuvants for oral immunization can be found in Vaccine Design, The Subunit and Adjuvant Approach, Powell and Newman (Eds.), Plenum Press, New York (1995).

"Administration of" and "administering a" compound should be understood to mean providing a compound, a prodrug of a compound, a conjugate of the compound, or a pharmaceutical composition that includes the compound as described herein. Administration may be for either "prophylactic" or "therapeutic" purpose. When provided prophylactically, compounds or compositions are provided in advance of any symptom. The prophylactic administration of the compound or composition serves to prevent or ameliorate any subsequent infection. When provided therapeutically, the compound or composition is provided at (or shortly after) the onset of a symptom of infection. The compound or composition may, thus, be provided prior to the anticipated exposure to B. anthracis so as to attenuate the anticipated severity, duration or extent of an infection and disease symptoms, after exposure or suspected exposure to these bacteria, or after the actual initiation of an infection. For all therapeutic, prophylactic and diagnostic uses, the polysaccharide-carrier conjugates, as well as antibodies and other necessary reagents and appropriate devices and accessories may be provided in kit form so as to be readily available and easily used.

Administration includes self-administration by a subject or administration to a subject by another person. Administered to a subject may be by a variety of mucosal administration modes, including by oral, rectal, intranasal, intrapulmonary, or transdermal delivery, or by topical delivery to other surfaces. Non-mucosal administration routes include intramuscular, subcutaneous, intravenous, intra-atrial, intra-articular, intra-peritoneal, or parenteral routes. Administration may be ex vivo by direct exposure to cells, tissues or organs originating from a subject.

Also included are kits, packages and multi-container units containing the pharmaceutical compositions, active ingredients, and/or means for administering the same for use in the prevention and treatment of anthrax and other bacterial diseases and other conditions in mammalian subjects. Kits for diagnostic use are also included. These kits may include a container or formulation that contains one or more of the polysaccharide, polysaccharide conjugate and/or other active agent described. In one example, the polysaccharide conjugate and/or other active agent described is formulated in a pharmaceutical preparation for delivery to a subject. The conjugates and/or other biologically active agent is/are optionally contained in a bulk dispensing container or unit or multi-unit dosage form. Optional dispensing means can be provided, for example a pulmonary or intranasal spray applicator. Packaging materials optionally include a label or instruction indicating for what treatment purposes (for example, anthrax) and/or in what manner the pharmaceutical agent packaged therewith can be used.

"Antibody" refers to immunoglobulin molecules and immunologically active portions of immunoglobulin molecules. Exemplary antibody molecules are intact immunoglobulin molecules, substantially intact immunoglobulin molecules, and portions of an immunoglobulin molecule, including those portions known in the art as Fab, Fab', F(ab')$_2$ and F(v), as well as chimeric antibody molecules.

In one aspect an antibody is characterized as comprising antibody molecules that immunoreact with B. anthracis spores. Antibodies are typically produced by immunizing a mammal with an immunogen or vaccine containing a B. anthracis saccharide-protein carrier conjugate to induce, in the mammal, antibody molecules having immunospecificity for the saccharide moiety. Antibody molecules having immunospecificity for the protein moiety will also be produced. The antibody molecules may be collected from the mammal and, optionally, isolated and purified by methods known in the art.

Human or humanized monoclonal antibodies are preferred, including those made by phage display technology, by hybridomas, or by mice with human immune systems. The antibody molecules may be polyclonal or monoclonal. Monoclonal antibodies may be prepared from murine hybridomas according to the classic method of Kohler et al. [Nature 256, 495-497, (1975)], or a derivative method thereof. Briefly, a mouse is repetitively inoculated with a few micrograms of the selected immunogen (for example, a polysaccharide conjugate) over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as the enzyme-linked immuno-absorbent assay (ELISA) or a derivative method thereof. Selected positive clones can be expanded and their monoclonal antibody product harvested for use. Detailed procedures for monoclonal antibody production are described in Harlow and Lane, Using Antibodies: A Laboratory Manual, CSHL, New York (1999). Polyclonal antiserum containing antibodies can be prepared by immunizing suitable animals with an immunogen comprising a polysaccharide conjugate.

Effective antibody production (whether monoclonal or polyclonal) is affected by many factors related both to the antigen and the host species. For example, small molecules tend to be less immunogenic than others and may require the use of carriers and adjuvants. Also, host animals vary in response to site of inoculations and dose, with either inadequate or excessive doses of antigen resulting in low titer antisera. Small doses (ng level) of antigen administered at multiple intradermal sites appear to be most reliable. An effective immunization protocol for rabbits can be found in Vaitukaitis et al. [*J. Clin. Endocrinol. Metab.* 33, 988-991 (1971)].

Antibodies may be contained in blood plasma, serum, hybridoma supernatants and the like. Antibody-containing serum will be capable of killing, in the presence of complement, 50% of *B. anthracis* bacilli or spores at a serum dilution of 1300:1 or more, typically will do so at a dilution of 32,000:1 or more, and most typically will be capable of killing 50% of *B. anthracis* bacilli or spores at a dilution of 64,000:1 or more.

Alternatively, the antibodies are isolated to the extent desired by well known techniques such as, for example, ion chromatography or affinity chromatography. The antibodies may be purified so as to obtain specific classes or subclasses of antibody such as IgM, IgG, IgA, $IgG_1$, $IgG_2$, $IgG_3$, $IgG_4$ and the like. Antibodies of the IgG class are preferred for purposes of passive protection.

"Antibody fragments" can be used in place of whole antibodies and can be readily expressed in prokaryotic host cells. Methods of making and using immunologically effective portions of monoclonal antibodies, also referred to as antibody fragments, are well known. Conditions by which a polypeptide/binding agent complex can form are known in the art.

The antibodies have a number of diagnostic and therapeutic uses. They are useful in prevention and treatment of infections and diseases caused by *B. anthracis*. They can also be used as in vitro diagnostic tools or assays to test for the presence of *B. anthracis* including in biological samples, in soil samples, in air, in water, in weapon components, in containers that may have been used to store weapons or weapon components, and carriers (e.g., human beings, animals, etc.) who may have been exposed to, or may be transporting *B. anthracis*.

Assays include, but are not limited to, agglutination assays, radioimmuno assays, enzyme-linked immunosorbent assays, fluorescence assays, Western blots and the like. In one such assay, for example, a sample containing *B. anthracis* is contacted with a first antibody describes, and a labeled second antibody is used to detect the presence of *B. anthracis* to which the first antibodies have bound. Such assays may be, for example, of direct format (where a labeled first antibody is reactive with the antigen), an indirect format (where a labeled second antibody is reactive with the first antibody), a competitive format (such as the addition of a labeled antigen), or a sandwich format (where both labeled and unlabelled antibodies are used), as well as other formats described in the art.

In providing antibodies to a recipient mammal, preferably a human, the dosage of administered antibodies will vary depending upon such factors as the mammal's age, weight, height, sex, general medical condition, previous medical history and the like. In general, it is desirable to provide the recipient with a dosage of antibodies which is in the range of from about 1 mg/kg to about 10 mg/kg body weight of the mammal, although a lower or higher dose may be administered. The antibodies are intended to be provided to the recipient subject in an amount sufficient to prevent, or lessen or attenuate the severity, extent or duration of the infection by *B. anthracis*. Antibodies which specifically immunoreact with HMB- and HB-linked saccharides are intended to be provided to the recipient subject in an amount sufficient to prevent, or lessen or attenuate the severity, extent or duration of the infection by *B. anthracis*.

An "analog" is a molecule, that differs in chemical structure from a parent compound, for example a homolog (differing by an increment in the chemical structure, such as a difference in the length of an alkyl chain), a molecular fragment, a structure that differs by one or more functional groups, or a change in ionization. Structural analogs are often found using quantitative structure activity relationships (QSAR), with techniques such as those disclosed in Remington: The Science and Practice of Pharmacology, 19th Edition, Chapter 28 (1995).

An "antigen" is a compound, composition, or substance that can stimulate an immune response, such as the production of antibodies or a T-cell response in an animal, including compositions that are injected or absorbed into an animal. An antigen reacts with the products of specific humoral or cellular immunity, including those induced by heterologous immunogens. The term "antigen" includes all related antigenic epitopes.

An "animal" is a living multi-cellular vertebrate organism, a category that includes, for example, mammals and birds. The term mammal includes both human and non-human mammals. Similarly, the term "subject" includes both human and veterinary subjects.

"Binding agents" can be used to purify and detect polysaccharides, as well as for detection and diagnosis of *B. anthracis* and anthrax. Examples of the binding agents are a polyclonal or monoclonal antibody (including humanized monoclonal antibody), and fragments thereof, that bind to any of the polysaccharides or polysaccharides conjugates disclosed. Binding agents may be bound to a substrate (for example, beads, tubes, slides, plates, nitrocellulose sheets, and the like) or conjugated with a detectable moiety, or both bound and conjugated. The detectable moieties can include, but are not limited to, an immunofluorescent moiety (for example, fluorescein, rhodamine), a radioactive moiety (examples include $^3H$, $^{32}P$, $^{35}S$, and $^{125}I$), an enzyme moiety (examples include horseradish peroxidase and alkaline phosphatase), a colloidal gold moiety, and a biotin moiety. Such conjugation techniques are standard in the art A "booster" refers to an increased immune response to an immunogenic composition upon subsequent exposure of the mammalian host to the same immunogenic composition. Booster injections can be given at regular intervals, and antiserum harvested when the antibody titer thereof, as determined semi-quantitatively, for example, by double immunodiffusion in agar against known concentrations of the antigen, begins to fall.

A "conjugate" is inclusive of any construct that includes an immunogenic compound coupled to a pharmaceutically acceptable carrier. Thus, "conjugate" is not limited to a conjugate of an immunogenic compound covalently bound to a protein carrier (which specific type of conjugate is often referred to in the art as a "conjugate vaccine").

"Cross-reactive" refers to the ability of an antibody to react with similar antigenic sites on different proteins. Cross-reactivity also comprises the ability of an antibody to react with or bind an antigen that did not stimulate its production, i.e., the reaction between an antigen and an antibody that was generated against a different but similar antigen.

A "derivative" is a biologically active molecule derived from a base molecular structure.

Immune response: A response of a cell of the immune system, such as a B cell, T cell, or monocyte, to a stimulus. In one example, the response is specific for a particular antigen (an "antigen-specific response"). In another example, an immune response is a T cell response, such as a $CD4^+$ response or a $CD8^+$ response. In yet another example, the response is a B cell response, and results in the production of specific antibodies.

The terms "immunoreact" and "immunoreactivity" refer to specific binding between an antigen or antigenic determinant-containing molecule and a molecule having an antibody combining site, such as a whole antibody molecule or a portion thereof.

An "immunogenic composition" or 'immunogenic agent' is any composition or agent that elicits an immune response in a mammalian host when the immunogenic composition or agent is injected or otherwise introduced. The immune response may be humoral, cellular, or both.

Inhibiting or Treating a Disease: Inhibiting refers to arresting the development of a disease or condition, for example, in a subject who is at risk for a disease such as anthrax. "Treating" or "treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

An "isolated" biological component is a component that has been substantially separated or purified away from other biological components in the cell of the organism in which the component naturally occurs, i.e., other chromosomal and extra-chromosomal DNA and RNA, proteins, lipids, and organelles. "Isolated" does not require absolute purity. For example, the desired isolated biological component may represent at least 50%, particularly at least about 75%, more particularly at least about 90%, and most particularly at least about 98%, of the total content of the preparation. Isolated biological components as described herein can be isolated by many methods such as salt fractionation, phenol extraction, precipitation with organic solvents (for example, hexadecyltrimethylammonium bromide or ethanol), affinity chromatography, ion-exchange chromatography, hydrophobic chromatography, high performance liquid chromatography, gel filtration, iso-electric focusing, physical separation (e.g., centrifugation or stirring), and the like.

"Label" is a detectable compound or composition that is conjugated directly or indirectly to another molecule to facilitate detection of that molecule. Specific, non-limiting examples of labels include fluorescent tags, enzymatic linkages, and radioactive isotopes.

"Lymphocytes" are a type of white blood cell that is involved in the immune defenses of the body. There are two main types of lymphocytes: B cells and T cells.

Pharmaceutically acceptable carriers: A "carrier" is a physiologically acceptable substance with which the therapeutically or biologically active compound disclosed herein is associated. The carrier may facilitate a certain type of administration of the therapeutically or biologically active compound and/or enhance the immune response induced by the therapeutically or biologically active compound. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. Remington's Pharmaceutical Sciences, by E. W. Martin, Mack Publishing Co., Easton, Pa., 15th Edition (1975), describes compositions and formulations suitable for pharmaceutical delivery of the BBGL-II herein disclosed.

"Pharmaceutically acceptable additive" is inclusive of any ingredient added or included in a pharmaceutical composition, including a pharmaceutically acceptable carrier, an adjuvant, or a therapeutically active agent.

"Polymeric carriers" are chosen to increase the immunogenicity of a polysaccharide and/or polysaccharide conjugate and/or to raise antibodies against the carrier which are medically beneficial. Carriers that fulfill these criteria have been described in the art. A polymeric carrier can be a natural or a synthetic material containing one or more functional groups, for example primary and/or secondary amino groups, azido groups, or carboxyl groups. The carrier can be water soluble or insoluble.

Water soluble peptide carriers are preferred, and include but are not limited to natural or synthetic polypeptides or proteins, such as bovine serum albumin, and bacterial or viral proteins or non-toxic mutants or polypeptide fragments thereof. Examples include tetanus toxin or toxoid, diphtheria toxin or toxoid, *P. aeruginosa* exotoxin or toxoid, recombinant *P. aeruginosa* exoprotein A (rEPA), *B. anthracis* protective antigen, recombinant *B. anthracis* protective antigen, pertussis toxin or toxoid, *Clostridium perfringens* exotoxin or toxoid, *C. welchii* exotoxin or toxoid, mutant non-toxic Shiga holotoxin, Shiga toxins 1 and 2, and the B subunit of Shiga toxins 1 and 2.

Examples of water insoluble carriers include, but are not limited to, aminoalkyl SEPHRAROSE, e.g., aminopropyl or aminohexyl SEPHAROSE (PHARMACIA Inc., Piscataway, N.J.), aminopropyl glass, and the like. Other carriers may be used when an amino or carboxyl group is added, for example through covalent linkage with a linker molecule. Additional polysaccharide carriers include, but are not limited to, dextran, capsular polysaccharides from microorganisms such as the Vi capsular polysaccharide from *S. typhi* (see, for example, U.S. Pat. No. 5,204,098, the contents of which are incorporated in their entirety by reference); *Pneumococcus* group 12 (12F and 12A) polysaccharides; *Haemophilus influenzae* type d polysaccharide; and certain plant, fruit, and synthetic oligo- or polysaccharides which are immunologically similar to capsular polysaccharides, such as pectin, D-galacturonan, oligogalacturonate, or polygalacturonate (for example, as described in U.S. Pat. No. 5,738,855, the contents of which are incorporated in their entirety by reference).

Methods for Attaching Polymeric Carriers: Attaching or linking polysaccharides to protein carriers confers enhanced immunogenicity and T-cell dependence. Methods for attaching a polysaccharide to a protein are well known in the art. For example, a polysaccharide containing at least one carboxyl group, through carbodiimide condensation, may be thiolated with cystamine, or aminated with adipic dihydrazide, diaminoesters, ethylenediamine and the like. Groups which can be introduced by such known methods include thiols, hydrazides, amines and carboxylic acids. Thiolated and aminated intermediates are stable, and may be freeze dried and stored cold. Thiolated intermediates may be covalently linked to a polymeric carrier containing a sulfhydryl group, such as a 2-pyridyldithio group. Aminated intermediates may be covalently linked to a polymeric carrier containing a carboxyl group through carbodiimide condensation.

The polysaccharide can be covalently bound to a carrier with or without a linking molecule. To conjugate without a linker, for example, a carboxyl-group-containing polysaccharide and an amino-group-containing carrier are mixed in the presence of a carboxyl activating agent, such as a carbodiimide, in a choice of solvent appropriate for both the polysaccharide and the carrier. The polysaccharide is often conjugated to a carrier using a linking molecule. A linker or cross-linking agent is preferably a small linear molecule having a molecular weight of about 500 or less, and is non-pyrogenic and non-toxic in the final product form.

To conjugate with a linker or cross-linking agent, either or both of the polysaccharide and the carrier may be covalently bound to a linker first. The linkers or cross-linking agents are homo-bifunctional or hetero-bifunctional molecules, e.g., adipic dihydrazide, ethylenediamine, cystamine, N-succinimidyl 3-(2-pyridyldithio)propionate (SPDP), N-succinimidyl-N-(2-iodoacetyl)-β-alaninate-propionate (SIAP), succinimidyl 4-(N-maleimido-methyl)cyclohexane-1-carboxylate (SMCC), 3,3'-dithiodipropionic acid, and the like. Also among the class of hetero-bifunctional linkers area ω-hydroxy and ω-amino alkanoic acids. Other linkers include amino acids, including amino acids capable of forming disulfide bonds, but can also include other molecules such as, for example, polysaccharides or fragments thereof. Linkers can be chosen so as to elicit their own immunogenic effect which may be either the same, or different, than that elicited by the polysaccharides and/or carriers disclosed herein. For example, such linkers can be bacterial antigens which elicit the production of antibodies to an infectious bacteria. In such instances, for example, the linker can be a protein or protein fragment of an infectious bacterium.

More specifically, attachment of a polysaccharide to a protein carrier can be accomplished by methods known to the art. Attachment may be accomplished by derivatized the protein carrier with adipic acid dihydrazide (ADH) via carbodiimide activation. The resulting product is reacted with the polysaccharide using 1-ethyl-3-[3-dimethylaminopropyl]carbodiimide (EDC). Other examples include derivatization with succinimidyl 3-(bromoacetamido) propionate (SBAP), succinimidylformylbenzoate (SFB), and succinimidyllevulinate (SLV).

Regardless of the precise method used to prepare the conjugate, after the coupling reactions have been carried out the unbound materials are removed by routine physicochemical methods, such as for example gel filtration or ion exchange column chromatography, depending on the materials to be separated. For example, a polysaccharide-protein conjugated product is dialyzed after the coupling reaction and purify by gel filtration using a SEPHAROSE CL-6B column. The final conjugate consists of a polysaccharide and a carrier bound directly or through a linker. Another method for purification involves ultra filtration in the presence of ammonium sulfate, as described in U.S. Pat. No. 6,146,902, the contents of which are incorporated in their entirety by reference. Alternatively a polysaccharide-carrier conjugate can be purified away from unreacted starting materials by any number of standard techniques including, for example, size exclusion chromatography, density gradient centrifugation, hydrophobic interaction chromatography, or ammonium sulfate fractionation. The compositions and purity of the conjugates can be determined by GLC-MS and MALDI-TOF spectrometry.

Complex structural characteristics determine optimal immunogenicity for the conjugates. The lengths and densities of the conjugate must be sufficient to occupy a cognate antibody combining site and determine the ability of the conjugate to form both aggregates with the surface receptor, and to permit interaction of the carrier fragments with T-cells. Conjugates typically have saccharide:carrier densities of about 5:1 to about 32:1; about 8:1 to about 22:1; and about 10:1 to about 15:1.

"Pharmaceutically acceptable complexes" complexes or coordination compounds formed from metal ions. Such complexes can include a ligand or chelating agent for bonding with an estrogenic agent.

"Pharmaceutically acceptable salts" of the presently disclosed compounds include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in Handbook of Pharmaceutical Salts, Properties, Selection and Use, Wiley VCH (2002).

"Pharmaceutical compositions" include therapeutic and prophylactic formulations of a polysaccharide conjugate and/or a polysaccharide-based immunogen typically combined together with one or more pharmaceutically acceptable vehicles and, optionally, other therapeutic ingredients (for example, antibiotics, or anti-inflammatories).

To formulate a pharmaceutical composition, a polysaccharide and/or polysaccharide conjugate can be combined with various pharmaceutically acceptable additives, as well as a base or vehicle for dispersion of the polysaccharide and/or the polysaccharide conjugate. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80), solubility enhancing agents (for example, cyclodextrins and derivatives thereof), stabilizers (for example, serum albumin), and reducing agents (for example, glutathione) can be included. One or more adjuvants may be included.

When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

A polysaccharide and/or polysaccharide conjugate can be dispersed in a base or vehicle, which can include a hydrophilic compound having a capacity to disperse the polysaccharide and/or polysaccharide conjugate, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and non-toxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including, fluid or viscous solutions, gels, pastes, powders, microspheres and films for direct application to a mucosal surface.

The polysaccharide and/or polysaccharide conjugate can be combined with the base or vehicle according to a variety of methods, and release of the polysaccharide and/or polysaccharide conjugate can occur by diffusion, disintegration of the vehicle, or associated formation of water channels. In some circumstances, the polysaccharide and/or polysaccharide conjugate is dispersed in microcapsules (microspheres) or nanocapsules (nanospheres) prepared from a suitable polymer, for example, isobutyl 2-cyanoacrylate, and dispersed in a biocompatible dispersing medium, which yields sustained delivery and biological activity over a protracted time.

Pharmaceutical compositions for administering a polysaccharide and/or polysaccharide conjugate can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the polysaccharides and/or polysaccharide conjugate can be brought about by including in the composition an agent which delays absorption, for example, monostearate salts and gelatin.

In certain aspects, the polysaccharide and/or polysaccharide conjugate can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When a controlled release formulation is desired, controlled release binders suitable for use include any biocompatible controlled release material which is inert to the active agent and which is capable of incorporating the polysaccharides and/or polysaccharide conjugate. Numerous such materials are known. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known to be biodegradable and to lead to degradation products having no or low toxicity. Exemplary polymers include polyglycolic acids and polylactic acids, poly(DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly($\epsilon$-caprolactone), poly($\epsilon$-aprolactone-CO-lactic acid), poly($\epsilon$-aprolactone-CO-glycolic acid), poly ($\beta$-hydroxy butyric acid), poly(alkyl-2-cyanoacrylate), hydrogels, such as poly(hydroxyethyl methacrylate), polyamides, poly(amino acids), for example, L-leucine, glutamic acid, L-aspartic acid and the like), poly(ester urea), poly(2-hydroxyethyl-DL-aspartamide), polyacetal polymers, polyorthoesters, polycarbonate, polymaleamides, polysaccharides, and copolymers thereof. Many methods for preparing such formulations are well known to those skilled in the art [see, for example, Sustained and Controlled Release Drug Delivery Systems, J. R. Robinson, Ed., Marcel Dekker, Inc., New York (1978)]. Other useful formulations include controlled-release microcapsules, lactic acid-glycolic acid copolymers useful in making microcapsules and other formulations and sustained-release compositions for water-soluble peptides.

The pharmaceutical compositions of the disclosure typically are sterile and stable under conditions of manufacture, storage and use. Sterile solutions can be prepared by incorporating the polysaccharides and/or polysaccharide conjugate in the required amount in an appropriate solvent with one or a combination of ingredients enumerated herein, as required, followed by filtered sterilization. Generally, dispersions are prepared by incorporating a polysaccharide and/or polysaccharide conjugate into a sterile vehicle that contains a basic dispersion medium and the required other ingredients from those enumerated herein. In the case of sterile powders, methods of preparation include vacuum drying and freeze-drying which yields a powder of the polysaccharide and/or polysaccharide conjugate plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

The term "purified" does not require absolute purity; rather, it is intended as a relative term. Thus, for example, a purified peptide preparation is one in which the peptide or protein is more enriched than the peptide or protein is in its natural environment within a cell. For example, a compound preparation is purified such that the desired polysaccharide protein conjugate represents at least 50%, more particularly at least about 90%, and most particularly at least about 98%, of the total content of the preparation.

"Subject" includes humans as well as non-human primates and other animals that are susceptible to an infection by *B. anthracis*.

"T Cell" is a white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. A CD8 T cells may be a cytotoxic T lymphocyte or a suppressor T cell.

"Therapeutically active agent" is an compound or composition that causes induction of an immune response, as measured by clinical response. Examples include increase in a population of immune cells, production of antibody that specifically binds, or measurable resistance to infection with *B. anthracis*. Therapeutically active agents can also include organic or other chemical compounds that mimic the effects of BBGL-II.

The term "unit dose" as it pertains to the inocula refers to physically discrete units suitable as unitary dosages for mammals, each unit containing a predetermined quantity of active material calculated to produce the desired immunogenic effect in association with the required diluent. Inocula are typically prepared as solutions in physiologically tolerable (acceptable) diluents such as water, saline, phosphate-buffered saline, or the like, to form an aqueous pharmaceutical composition. Adjuvants, such as aluminum hydroxide, may also be included in the compositions. The route of inoculation may be intramuscular, subcutaneous or the like, which results in eliciting antibodies protective against *B. anthracis*. In order to increase the antibody level, a second, or booster, dose may be administered approximately 4 to 6 weeks after the initial injection. Subsequent doses may be administered as indicated herein, or as desired by the practitioner.

"Vaccine" is an antigen that elicits an immune response that results in a decrease in anthrax burden of a least about 30% in a subject in relation to a non-vaccinated (e.g., adjuvant alone) control subject. Preferably, the level of the decrease is about 50%, and most preferably, about 60 to about 70% or greater.

"Vaccination" refers to eliciting an immune response in a subject by administration of a vaccine. The quantity to be administered depends upon factors such as the age, weight and physical condition of the subject considered for vaccination. The quantity also depends upon the capacity of the subject's immune system to synthesize antibodies, and the degree of protection desired. Effective dosages can be readily established by one of ordinary skill in the art through routine trials establishing dose response curves.

Dosage for Vaccination: An inoculum contains an effective, immunogenic amount of a polysaccharide and/or polysaccharide-carrier conjugate. The effective amount of a polysaccharide and/or polysaccharide-carrier conjugate per unit dose sufficient to induce an immune response to *B. anthracis* spores depends, among other things, on the species of mammal inoculated, the body weight of the mammal, and the chosen inoculation regimen, as is well known in the art. Inocula typically contain a polysaccharide and/or polysaccharide-carrier conjugates with concentrations of polysaccharide from about 1 micrograms to about 10 milligrams per inoculation (dose), about 3 micrograms to about 100 micrograms per dose, and most about 5 micrograms to 50 micrograms per dose.

The descriptions are provided solely to aid the reader, and should not be construed to have a scope less than that understood by a person of ordinary skill in the art or as limiting the scope of the appended claims. Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for compounds are approximate, and are provided for description. Although methods and materials similar or equivalent to those described herein can be used in the practice or testing of this disclosure, suitable methods and materials are described below. The term "comprises" means "includes". In addition, the materials, methods, and examples are illustrative only and not intended to be limiting. All chemical compounds disclosed herein include both the (+) and (−) stereoisomers, either the (+) or (−) stereoisomer, and/or any tautomers thereof, unless the context indicates otherwise or the description states otherwise.

One significant unknown during a deliberate or accidental release of *B. anthracis* is which part of *B. anthracis* has entered the host. While *B. anthracis* spores are the infectious agent, ingestion of the anthrax toxin also causes anthrax. With respect to the *B. anthracis* spores, they can be mutated to form virulent (e.g., the Ames strain) or non-virulent varieties (e.g., the Sterne strain). Ideally therefore, the development of anthrax vaccines would occur over a broad front, i.e., use different spore proteins to generate a wide variety of vaccines. Vaccines that recognize different immuno-dominant spore proteins are most useful because if one does not work, another can be administered. The BclA glycoprotein is merely one of many possible immuno-dominant spore proteins that can be used to develop anthrax vaccines.

The BclA tetrasaccharide has the structure 2-O-methyl-4-(3-hydroxy-3-methylbutanamido)-4,6-dideoxy-β-D-glucose-(1→3)-α-L-rhamnopyranosyl-(1→3)-α-L-rhamnopyranosyl-(1→2)-L-rhamnopyranose, as shown next:

anthrose which can also be represented by

3)-α-L-Rhap-(1-3)-α-L-Rhap-(1-2)-L-Rha

The anthrose portion is thought to be the immunodominant part of the BclA tetrasaccharide. Mehta et al., *Chem. Eur. J.* 12, 9136-9149 (2006), synthesized the BclA tetrasaccharide, along with a series of analogs, and determined that the 3-methyl-butyryl chain of the anthrose sugar is an important antigenic component of the tetrasaccharide. In other words, the 3-methyl group appears to be the most important while the 3-hydroxyl group appears not to be important. However, Wang et al., *Proteomics* 7, 180-184 (2007), determined that the anthrose monosaccharide is marginally reactive while the anthrose-containing tetrasaccharide is highly reactive.

From the current scientific data, it appears that: (1) the BclA tetrasaccharide is unique to *B. anthracis*; (2) the 3-methyl-butyryl chain of the anthrose sugar is the important antigenic component of the tetrasaccharide; and (3) the remaining trisaccharide portion of BclA is also important. In other words, according to the current scientific data, any anthrax vaccines developed using BclA as the antigen require both anthrose and the three rhamnose saccharides. Furthermore, because the BclA tetrasaccharide is unique to *B. anthracis*, development of these vaccines must use anthrax spores or portions thereof.

Separation and purification of the BclA tetrasaccharide from the thousands of proteins in the *B. anthracis* spore is an extensive process and the overall yield is low. Moreover, working with anthrax spores is difficult and can be dangerous. Alternatively, the BclA tetrasaccharide can be synthesized. However, synthetic preparation of the BclA tetrasaccharide is expensive and the yields are also low. Therefore, compounds similar to the BclA tetrasaccharide is useful. Also useful is a source of compounds similar to the BclA tetrasaccharide, a source that is easy to grow and from which compounds similar to the BclA tetrasaccharide can be harvested.

*Shewanella* is a Gram-negative bacterium that lives in aquatic and sub-surface environments. *Shewanella* spp. strain MR-4 is a metabolically versatile bacterium that can use a diversity of organic compounds and metals to obtain energy needed for growth and survival. *Shewanella* is related to *Escherichia*; therefore, tools and techniques developed for *Escherichia* work with *Shewanella*. *Shewanella* also has the ability to tolerate oxygen, which is a useful ability that makes it easier to work with in the laboratory. Vinogradov et al., *Carbohydrate Res.* 340, 1750-1753 (2005), analyzed the capsular polysaccharides of *Shewanella* spp. MR-4. They determined that the capsular polysaccharides had a regular structure with a repeating unit of five monosaccharides: 4-amino-4,6-dideoxy-α-glucopyranose; α-glucopyranosyluronic acid; β-mannopyranose; N-acetyl-β-glucosamine; and β-glucopyranose. The structure of the repeating unit is shown next. The number of the repeating units is variable and can depend upon the growing conditions. In general, based on the gel filtration profile, the molecular size of the capsular polysaccharide is between about 20 to about 500 kDa, and thus it contains about 20 to about 500 repeating units.

The repeating unit also includes either 3-hydroxy-3-methylbutyrate (HMB) or 3-hydroxy-butyrate (HB). HMB and HB are commonly found in most organisms, including bacteria. For example, HMB is a metabolite of leucine and a precursor of cholesterol. While there are a number of known bacterial polysaccharides containing HB, bacterial polysaccharides containing HMB are much rarer. In the repeating capsular polysaccharide of *Shewanella* spp. MR-4, HMB or HB is found linked to the 4-amino-group of the terminal α-glucopyranose saccharide. Whether the capsular polysaccharide contained HMB or HB depends on the medium on which *Shewanella* spp. MR-4 was grown.

Structurally, the capsular polysaccharides of *Shewanella* spp. MR-4 are substantially different from the BclA tetrasaccharide of *B. anthracis*. While it is true that both contain HMB (or the related HB), the sugar moieties are very different. This is not surprising because *Shewanella* and *B. anthracis* are significantly different organisms. For example, one significant difference is that *B. anthracis* is infectious while *Shewanella* is benign. It is likely therefore that the function of the surface polysaccharides in *B. anthracis* is different from those in *Shewanella*.

HMB-Substituted Capsular Polysaccharide from *Shewanella* Spp. MR-4

HB-Substituted Capsular Polysaccharide from *Shewanella* Spp. MR-4

BclA Tetrasaccharide from *B. anthracis*

The molecular size of the HMB-substituted capsular polysaccharide or the HB-substituted capsular polysaccharide can range from 5 to 5000, preferably 20 to 500 kDa, and the number of repeating units can range from 5 to 5000, preferably 20 to 500.

The immunogenicity of saccharides, alone or as protein conjugates, is related to several variables: 1) species and the age of the recipient; 2) molecular weight of the saccharide; 3) density of the saccharide on the protein; 4) configuration of the conjugate (single vs. multiple point attachment); and 5) the immunologic properties of the protein.

In other words, one of ordinary skill in the art would not expect that HMB-substituted capsular polysaccharide from Shewanella would be a suitable antigen for the development of vaccines against B. anthracis. As noted previously, both the entire anthrose monosaccharide (i.e., not just the HMB group, which is a common compound and found in other bacterial polysaccharides) and the three rhamnose saccharides are important for a fully-reactive B. anthracis antigen. Therefore, one of ordinary skill in the art would not expect that antibodies raised against the HMB-substituted capsular polysaccharide from Shewanella would be reactive towards B. anthracis spores. One of ordinary skill in the art would also not expect that antibodies raised against the HB-substituted capsular polysaccharide from Shewanella would be reactive towards B. anthracis spores. The HB-substituted capsular polysaccharide from Shewanella lacks both the 3-methyl group and the three rhamnose saccharides—both of which have been shown to be important.

Furthermore, because the 3-methyl group is known to be important, one of ordinary skill in the art would also not expect that other HB-capsular polysaccharides would be suitable antigens for anthrax vaccines. Indeed, thousands of HB-linked polysaccharides are known and none of them have been shown to be effective antigens for anthrax vaccines.

Pseudomonas syringae is a Gram-negative, flagellated, bacterium. It is a plant pathogen that can infect a wide variety of species. The bacterial flagella are primarily composed of flagellin. The glycosylation pattern of the flagellin is species-dependent. The glycosylated flagellin of P. syringae pv. tabacci comprises HB and two rhamnose monosaccharides (2-O-methyl-4-(3-hydroxy-butanamido)-4,6-dideoxy-β-D-glucose-(1→3)-α-L-rhamnopyranosyl-(1→2)-L-rhamnopyranosyl-1-O-serine) as shown next:

$$H_3C\text{—}H_3C\text{—}CH(OH)\text{—}C(O)\text{—}NH\text{—}[\text{sugar with } H_3C, HO, OCH_3]\text{—}3)\text{-}\alpha\text{-L-Rhap-(1-2)-}\alpha\text{-L-Rhap-(1-O-Ser)}$$

P. syringae Flagellin Glycan

The P. syringae flagellin glycan differs from the B. anthracis BclA tetrasaccharide in several ways. One, the B. anthracis BclA tetrasaccharide contains HMB while the P. syringae flagellin glycan contains HB. Two, the B. anthracis BclA tetrasaccharide contains three rhamnose monosaccharides while the P. syringae flagellin glycan contains two rhamnose monosaccharides. Three, the linkage between the first and second rhamnose monosaccharides in the B. anthracis BclA tetrasaccharide is 1→3, while in the P. syringae flagellin glycan it is 1→2. Four, the P. syringae flagellin glycan contains an O-linked serine, while the B. anthracis BclA tetrasaccharide is thought to link to the protein through a GalNAc moiety. Therefore, one of ordinary skill in the art would not expect that antibodies raised against the P. syringae flagellin glycan would be reactive towards B. anthracis spores.

The saccharides described herein may be isolated from Shewanella MR-4 or P. syringae or they may be synthesized.

In certain embodiments, the saccharides described above can be coupled to a carrier to form an immunogenic conjugate. For example, the HMB-substituted capsular polysaccharide from Shewanella MR-4, the HB-substituted capsular polysaccharide from Shewanella MR-4, and/or the P. syringae flagellin glycan can be covalently linked to a polymeric carrier to form an immunogenic conjugate. The carrier can be covalently linked to the saccharide structure via a carboxyl group or an amino group present on at least one of the monosaccharide units via conjugation methods as described above.

In certain embodiments, the saccharide(s) described above can be administered to a subject without conjugation to a carrier. For example, the pharmaceutical composition may include at least one of the saccharides and at least one pharmaceutically acceptable additive. In another example, the saccharide(s) can be administered without any other additive.

In another embodiment, killed whole cells of Shewanella MR-4 or P. syringae that includes the saccharides may be administered to the subject, particularly to non-human animals. Generally, the first step in making such a killed whole cell vaccine is to isolate or create an organism, or part of one, that is unable to cause the disease, but that still retains the antigens responsible for inducing the host's immune response. This can be done in many ways. One way is to kill the organism using heat or formalin; vaccines produced in this way are also called "inactivated" or "killed" vaccines. The killed whole cells Shewanella MR-4 or P. syringae are particularly useful for administration to non-human animal subjects such as cows that contact anthrax.

According to another embodiment, only a B. anthracis antigenic component of Shewanella MR-4 or P. syringae flagellin, for example the isolated capsule of Shewanella MR-4, or the isolated fimbriae of P. syringae, is administered to the subject (these types of vaccines are also known as "acellular vaccines"). Acellular vaccines exhibit some similarities to killed vaccines: neither killed nor acellular vaccines generally induce the strongest immune responses and may therefore require a "booster" every few years to insure their continued effectiveness.

The mechanics of immune response are unpredictable. Compounds that appear similar physically or chemically elicit widely varied immune responses. Furthermore, antibodies raised against one antigenic compound often do not recognize physically- or chemically-similar antigenic compounds. It is therefore unexpected that antibodies raised against HMB-substituted capsular polysaccharide from Shewanella, HB-substituted capsular polysaccharide from Shewanella, and the P. syringae flagellin glycan would recognize and react with spores of B. anthracis. It is also unexpected that antibodies raised against B. anthracis spores would recognize and react with the HMB-substituted capsular polysaccharide from Shewanella, the HB-substituted capsular polysaccharide from Shewanella, or the P. syringae flagellin glycan.

An HMB- or HB-saccharide-based vaccine is intended for active immunization, for prevention of anthrax infection, and for preparation of immune antibodies as a therapy, preferably for established infections. In one aspect, the vaccines are designed to confer specific preventative immunity against infection with anthrax, and to induce antibodies specific to B. anthracis spores. The anthrax vaccine may be composed of non-toxic components therefore making it suitable for infants, children of all ages, and adults.

The conjugates and/or compositions thereof, as well as the antibodies thereto, will be useful in increasing resistance to, preventing, ameliorating, and/or treating anthrax infection in humans, and in reducing or preventing anthrax in humans.

Also provided is a method for screening compounds against *B. anthracis* spores, the method comprising providing a compound selected from:

$$\text{H}_3\text{C}-\text{C}(\text{CH}_3)(\text{OH})-\text{CH}_2-\text{C}(=\text{O})-\text{NH}-\text{[sugar]}-4)\text{-}\alpha\text{-D-GlcA-(1-3)} \quad \text{with} \quad -4)\text{-}\beta\text{-D-Man-(1-4)-}\beta\text{-D-Glc-1-3-}\beta\text{-D-GlcNAc-(1-,}$$

$$\text{H}_3\text{C}-\text{C}(\text{CH}_3)(\text{OH})-\text{CH}(\text{OH})-\text{C}(=\text{O})-\text{NH}-\text{[sugar]}-4)\text{-}\alpha\text{-D-GlcA-(1-3)} \quad \text{with} \quad -4)\text{-}\beta\text{-D-Man-(1-4)-}\beta\text{-D-Glc-1-3-}\beta\text{-D-GlcNAc-(1-} \quad \text{or}$$

$$\text{H}_3\text{C}-\text{C}(\text{CH}_3)(\text{OH})-\text{CH}_2-\text{C}(=\text{O})-\text{NH}-\text{[sugar, OCH}_3\text{]}-3)\text{-}\alpha\text{-L-Rhap-(1-2)-}\alpha\text{-L-Rha-(1-O-Ser)}$$

adding an antibody that is immuno-reactive with a *B. anthracis* spore; and determining a level of reactivity of the compound with the antibody.

Compositions provided include, but are not limited to, mammalian serum, plasma, and immunoglobulin fractions, which contain antibodies which are immuno-reactive with anthrax spores, and which preferably also contain antibodies which are immuno-reactive with the BclA tetrasaccharide, the BclA glycoprotein, anthrose, anthrose-linked polysaccharides, HMB-linked saccharides, and HB-linked saccharides. These compositions, in the presence of complement, have bacteriostatic or bactericidal activity against *B. anthracis*. These antibodies and antibody compositions are useful to prevent, treat, or ameliorate infection and disease caused by *B. anthracis*. Antibodies in isolated form are also included.

High titer anti-anthrose sera, or antibodies isolated therefrom, could be used for therapeutic treatment for patients with *B. anthracis* infection. Antibodies elicited by the conjugates described may be used for the treatment of established anthrax infections, and are also useful in providing passive protection to an individual exposed to *B. anthracis* spores. For example, the sera could be administered to a subject to induce passive immunization against *B. anthracis*.

Also included are diagnostic tests and/or kits for anthrax infection and/or colonization, using the conjugates and/or antibodies, or compositions thereof.

Routine immunization schedule of infants and children, and in individuals at risk for anthrax infection is included. Use for intervention in epidemics and terrorist attacks caused by *B. anthracis* is also included. Conjugates may be used as components of multivalent vaccines for *B. anthracis* and other pathogens that contain HMB- or HB-linked saccharides. Conjugates may be used in diagnostic test for anthrax infection and/or colonization.

In accordance with various treatment methods, a polysaccharide and/or polysaccharide conjugate can be delivered to a subject in a manner consistent with conventional methodologies associated with management of the disorder for which treatment or prevention is sought. Typical subjects intended for treatment with the compositions and methods of the present disclosure include humans, as well as non-human primates and other animals. To identify subjects for prophylaxis or treatment according to the methods of the disclosure, accepted screening methods are employed to determine risk factors associated with a targeted or suspected disease of condition (for example, anthrax) as discussed herein, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods, which are available and well known in the art to detect and/or characterize disease-associated markers. These and other routine methods allow the clinician to select patients in need of therapy using the methods and pharmaceutical compositions of the disclosure. In accordance with these methods and principles, a polysaccharide and/or polysaccharide conjugate can be administered according to the teachings herein as an independent prophylaxis or treatment program, or as a follow-up, adjunct or coordinate treatment regimen to other treatments, including surgery, vaccination, immunotherapy, hormone treatment, cell, tissue, or organ transplants, and the like.

For prophylactic and therapeutic purposes, the polysaccharide and/or polysaccharide conjugate can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the polysaccharide and/or polysaccharide conjugate can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, non-human primate, and other accepted animal model subjects known. Alternatively, effective dosages can be determined using ice vitro models (for example, immunologic and histopathologic assays). Using such models, only ordinary calculations and adjustments are required to determine an appropriate concentration and dose to administer a therapeutically effective amount of the polysaccharide and/or polysaccharide conjugate (for example, amounts that are effective to elicit a desired immune response or alleviate one or more symptoms of a targeted disease). Alternatively, an effective amount or effective dose of the polysaccharide and/or polysaccharide conjugate may simply inhibit or enhance one or more selected biological activities correlated with a disease or condition, as set forth herein, for either therapeutic or diagnostic purposes.

The actual dosage of the polysaccharide and/or polysaccharide conjugate will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the polysaccharide and/or polysaccharide conjugate for eliciting the desired activity or biological response in the subject. Dosage regimens can be adjusted to provide an optimum prophylactic or therapeutic response. A therapeutically effective amount is also one in which any toxic or detrimental side effects of the polysaccharide and/or polysaccharide conjugate is outweighed in clinical terms by therapeutically beneficial effects. A non-limiting range for a therapeutically effective amount of a polysaccharide and/or polysaccharide conjugate is about 0.01 mg/kg body weight to about 10 mg/kg body weight, such as about 0.05 mg/kg to about 5 mg/kg body weight, or about 0.2 mg/kg to about 2 mg/kg body weight. Antibodies will typically be administered in a dosage ranging from about 1 mg/kg body weight to about 10 mg/kg body weight of the subject, although a lower or higher dose can be administered.

Upon administration of a polysaccharide and/or polysaccharide conjugate, for example, via injection, aerosol, oral, topical or other route, the immune system of the subject typically responds to the immunogenic composition by producing antibodies specific for the polysaccharide and/or polysaccharide conjugate. Such a response signifies that an immunologically effective dose of the polysaccharide and/or polysaccharide conjugate or related immunogenic composition was delivered. An immunologically effective dosage can be achieved by single or multiple administrations (including, for example, multiple administrations per day), daily, or weekly administrations. For each particular subject, specific dosage regimens can be evaluated and adjusted over time according to the individual need and professional judgment of the person administering or supervising the administration of the polysaccharides and/or polysaccharide conjugates. In some aspects, the antibody response of a subject administered the compositions of the disclosure will be determined in the context of evaluating effective dosages/immunization protocols. In most instances it will be sufficient to assess the antibody titer in serum or plasma obtained from the subject. Decisions as to whether to administer booster inoculations and/or to change the amount of the composition administered to the individual can be at least partially based on the antibody titer level. The antibody titer level can be based on, for example, an immuno-binding assay which measures the concentration of antibodies in the serum which bind to a specific antigen, for example, polysaccharide and/or polysaccharide conjugate. The ability to neutralize in vitro and in vivo biological effects of the B. anthracis can also be assessed to determine the effectiveness of the treatment.

Dosage can be varied by the attending clinician to maintain a desired concentration at a target site (for example, the lungs or systemic circulation). Higher or lower concentrations can be selected based on the mode of delivery, for example, transepidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth. To achieve the same serum concentration level, for example, slow-release particles with a release rate of 5 nanomolar (under standard conditions) would be administered at about twice the dosage of particles with a release rate of 10 nanomolar.

The methods of using polysaccharides and/or polysaccharide conjugates, and the related compositions and methods, are useful in increasing resistance to, preventing, ameliorating, and/or treating infection and disease caused by bacilli in animal hosts, and other, in vitro applications. The methods and compositions are useful in increasing resistance to, preventing, ameliorating, and/or treating infection and disease caused by B. anthracis infection in animals and humans. These immunogenic compositions can be used for active immunization for prevention of B. anthracis infection, and for preparation of immune antibodies. Immunogenic compositions and methods are typically designed to confer specific immunity against infection with B. anthracis, and to induce antibodies specific to B. anthracis polysaccharides and/or polysaccharide conjugates. The immunogenic compositions are composed of non-toxic components, suitable for infants, children of all ages, and adults.

The methods are broadly effective for treatment and prevention of bacterial disease and associated inflammatory, autoimmune, toxic (including shock), and chronic and/or lethal sequelae associated with bacterial infection. One or more symptoms or associated effects of exposure to and/or infection with anthrax may be prevented or treated by administration to a mammalian subject at risk of acquiring anthrax, or presenting with one or more anthrax symptom(s), of an effective amount of a polysaccharide and/or polysaccharide conjugate. Therapeutic compositions and methods of the disclosure for prevention or treatment of toxic or lethal effects of bacterial infection are applicable to a wide spectrum of infectious agents. Non-lethal toxicities that will be ameliorated by these methods and compositions can include fatigue syndromes, inflammatory/autoimmune syndromes, hypoadrenal syndromes, weakness, cognitive symptoms and memory loss, mood symptoms, neurological and pain syndromes and endocrine symptoms. Any significant reduction or preventive effect of the polysaccharide and/or polysaccharide conjugate with respect to the foregoing disease condition(s) or symptom(s) administered constitutes a desirable, effective property of the subject composition/method of the disclosure.

The compositions and methods are particularly useful for treatment and prevention of infection and toxic/morbidity effects of exposure to anthrax and/or other disease- or illness-causing bacilli. Also included are diagnostic compositions and methods to identify individuals at risk for exposure, infection, toxic effects, or long term deleterious effects of exposure to pathogenic bacteria, for example B. anthracis. The methods and compositions are useful for identification of environmental agents, including B. anthracis and other bacilli expressing a polysaccharide and/or polysaccharide conjugate, including food-borne pathogenic bacilli. Certain individuals exposed to small amounts of bacterial products, such as those derived from B. anthracis, presenting certain genetic or physiological backgrounds, are predisposed to development of chronic syndromes, including fatigue syndromes, inflammatory/autoimmune syndromes, hypoadrenal syndromes, weakness, cognitive symptoms and memory loss, mood symptoms, neurological and pain syndromes and endocrine symptoms. In this context, the methods and compositions of the disclosure are employed to detect, and alternatively to treat and/or ameliorate, such ubiquitous environmental exposures and associated symptoms. For example, antibodies provide for screening for polysaccharides and/or polysaccharide conjugates in mammalian subjects or food products at risk of contact/infection with a *Bacillus* that expresses a polysaccharide and/or polysaccharide conjugate.

Also provided are compositions, including but not limited to, mammalian serum, plasma, and immunoglobulin fractions, which contain antibodies that are immuno-reactive with a polysaccharide and/or polysaccharide conjugate of *B. anthracis* or another *Bacillus* species or strain. These antibodies and antibody compositions can be useful to prevent, treat, and/or ameliorate infection and disease caused by the microorganism. The disclosure also provides such antibodies in isolated form. High titer anti-polysaccharide and/or anti-polysaccharide conjugate sera, antibodies isolated therefrom, or monoclonal antibodies, can be used for therapeutic treatment for patients with infection by *B. anthracis* or another *Bacillus* species or strain. Antibodies elicited can be used for the treatment of established *B. anthracis* or other *Bacillus* infections, and can also be useful in providing passive protection to an individual exposed to *B. anthracis* or another *Bacillus*.

The following examples are exemplary of the present processes and incorporate suitable process parameters for use herein. These parameters may be varied, however, and the following should not be deemed limiting.

Example 1

Preparation of *Shewanella* Polysaccharides

This example describes the preparation of HMB- and HB-substituted capsular polysaccharides from *Shewanella* spp. MR-4.

*Shewanella* sp. strain MR-4 was grown in either Triptic Soy Broth (TSB, DIFCO Laboratories) or in chemically defined medium (CDM), prepared as described in Vinogradov et al., for 20 h at 25° C. with stifling and aeration; the pH was maintained at 7.2. The capsular polysaccharides were isolated from cell surface by vigorous shaking and purified. They were ultracentifuged at 35,000 rpm, for 5 h at 5° C. to remove lipo-polysaccharide contamination. The supernatant was lyophilized and then passed through a SEPHAROSE CL-6B column (1×100 cm) in 0.2 M NaCl. Two products were obtained depending on which medium was used for bacterial growth. *Shewanella* sp. grown on TSB produced predominantly HMB-substituted capsular polysaccharides while *Shewanella* sp. grown on CDM produced predominantly HB-substituted capsular polysaccharides. The chemical structures of the capsular polysaccharides were confirmed by NMR experiments. The sugar concentration was measured by the phenol/$H_2SO_4$ assay.

Example 2

Preparation of *Shewanella* Polysaccharide-Protein Conjugates

This example describes the preparation of protein conjugates using HMB- and HB-capsular polysaccharides from *Shewanella* obtained as described in Example 1.

To form a protein conjugate of the substituted capsular polysaccharides, bovine serum albumin (BSA) was first derivatized with adipic acid dihydrazide (ADH) via carbodiimide activation. Protein concentration was measured by the method of Lowry [*J. Biol. Chem.* 193, 265-275 (1951)]; hydrazide concentration by the TNBS assay [Schneerson et al., *J. Exp. Med.* 152, 361-376 (1980)]. The product (BSA-AH) contained adipic acid hydrazide groups. HMB- or HB-substituted capsular polysaccharide (10 mg) was dissolved in 1 ml of 0.2 M NaCl and the pH was adjusted to 5.5. 10 mg of BSA-AH was added in 0.5 ml of 0.2 M NaCl, followed by 1-ethyl-3-[3-dimethylaminopropyl]carbodiimide (EDC) to obtain a final concentration of EDC as 0.1 M. The reaction was carried out under automatic titrator at pH 5.5 for 4 h at room temperature. The product was dialyzed against 0.2 m NaCl overnight at 4° C. and purified by gel filtration using SEPHAROSE CL-6B column (1×100 cm) in 0.2 M NaCl. The conjugates were designated BSA/$CPS_{TSB}$ (HMB-substituted polysaccharide-protein conjugate) or BSA/$CPS_{CSM}$ (HB-substituted polysaccharide-protein conjugate).

Example 3

Recognition of Polysaccharide-Protein Conjugates by Anti-Anthrax Antibodies

This example shows that HMB- and HB-capsular polysaccharides are recognized by antibodies against whole anthrax spores (anti-spore) and against synthetic anthrax spore trisaccharide-KLH conjugate (anti-sacch).

5- to 6-week-old female NIH Swiss Webster mice were injected subcutaneously 3 times at 2 weeks intervals with 2.5 μg of either the BSA/$CPS_{TSB}$ conjugate or the BSA/$CPS_{CSM}$ conjugate in 0.1 ml phosphate buffered saline (PBS). Controls received PBS. Groups of 10 mice were exsanguinated 7 days after the third injections. Hyperimmune sera against *Shewanella* sp. MR-4 were prepared with heat-killed whole bacteria.

Double immunodiffusion were performed in 1% agarose gel in PBS. Antibody levels to the *Shewanella* capsular polysaccharides were measured by ELISA using Nunc chemically modified COVALINK plates. Plates were coated with either $CPS_{TSB}$ or $CPS_{CMP}$ (5 μg/ml) dissolved in 10 mM 1-methylimidazole buffer (pH 7.0) and EDC added to a final concentration of 50 mM. The antigens were applied at 100 μl per well and incubated at 37° C. overnight. Plates were washed 6 times with 0.1% Brij 35-saline and blocked with 1% HSA in PBS for 1 h at room temperature. Two-fold dilutions of anti-spore or anti-sacch sera were made in 1% HSA-0.1% Brij 35-saline and incubated at 37° C. for 4 h. Plates were washed, goat anti-mouse IgG conjugated to alkaline phosphatase was added, and the plates were incubated at 37° C. for 3 h. 4-Nitrophenylphosphate (1 mg/ml in 1 M Tris-HCl buffer, pH 9.8, containing 0.3 mM $MgSO_4$) was added, and the absorption at 405 nm ($A_{405}$) was read after 30 min in an MR600 microplate reader (Table 1).

TABLE 1

Serum dilution that gave $A_{405}$ of IgG titer in the ELISA assay

| Coating antigen | IgG titers* | |
|---|---|---|
| | Anti-spore | Anti-saccharide |
| $CPS_{TSB}$ | 1600 | 12800 |
| $CPS_{CMP}$ | 3200 | 500 |

B. anthracis Ames 35 strain (pXO1+ pXO2−) was grown on nutrient sporulation agar at 37° C. for 2 days. Spores were purified by washing the agar plate with deionized water and incubating the spore suspension at 65° C. for 30 min. After heat treatment, the spore suspension was washed twice with deionized water before fluorescent staining. Immunofluorescent staining was performed as follows. Spores were put on 1% polylysin-treated cover slip, and blocked in 3% milk in PBS for 30 min. Spores were stained with primary mice antibodies for 30 min. After three washes in PBS, the coverslips were treated with a secondary antibody, AF488 conjugate anti-mouse. After staining, coverslips were mounted to slides and they were examined by a Nikon fluorescent microscope.

Both the anti-spore and the anti-sacch precipitated both $CPS_{TSB}$ and $CPS_{CDM}$ in the immunodiffusion assay, as shown in FIG. 1. In another experiment microtiter plates were coated with $CPS_{TSB}$ or $CPS_{CDM}$ and an ELISA assay was performed. Table 2 shows that anti-sacch serum recognized $CPS_{TSB}$ better then $CPS_{CDM}$, but the anti-spore sera recognized $CPS_{CDM}$ better. The first result was in agreement with structural data since anti-trisaccharide serum was raised against anthrose, which was substituted with HMB group, as in $CPS_{TSB}$. This group was almost not present in $CPS_{CDM}$.

The BSA/$CPS_{TSB}$ conjugate induce higher level of antibodies to $CPS_{TSB}$ than to $CPS_{CDM}$ (54 vs. 43 EU) but the difference was not statistically significant. Similarly, there was no statistical difference in antibody levels induced by the BSA/$CPS_{TSB}$ conjugate while tested against either of $CPS_{TSB}$ or $CPS_{CDM}$ (31 vs. 32 EU).

TABLE 2

Composition and levels of mouse IgG of anti-Shewanella MR-4 CPS induced by conjugates of $CPS_{TSB}$ and $CPS_{CDM}$ bound to BSA.

| Conjugate | Protein:Sugar ratio (wt:wt) | ELISA Units after $3^{rd}$ injection Coating antigen | |
|---|---|---|---|
| | | $CPS_{TSB}$ | $CPS_{CDM}$ |
| BSA/$CPS_{TSB}$ | 2:1 | 54 | 43 |
| BSA/$CPS_{CDM}$ | 1:1.4 | 31 | 32 |

Mice (10 per group) were injected with 2.5 μg of saccharide as a conjugate per mouse, s.c., 3 times, 2 weeks apart and bled one week after last injection. Antibody levels were calculated relative to the hyperimmune mouse serum and assigned a value of 100 ELISA Units (EU).

Example 4

Recognition of *P. syringae* Bacteria by *B. anthracis* Spore Antibodies

This example shows that serum antibodies raised against *B. anthracis* spores recognize the *P. syringae* bacteria.

*P. syringae* bacteria were recognized by anti-*B. anthracis* spore serum by fluorescent microscopy, confirming the cross-reactivity with the spores.

Example 5

Recognition of *Shewanella* sp. MR-4 by *B. anthracis* Spore Antibodies

This example shows that serum antibodies raised against *B. anthracis* spores recognize the *Shewanella* sp. MR-4 bacteria.

*Shewanella* sp. MR-4 bacteria were recognized by anti-*B. anthracis* spore serum by fluorescent microscopy, confirming the cross-reactivity with the spores.

Example 6

Recognition of *B. anthracis* Spores by *Shewanella* Polysaccharide Antibodies

This example shows that serum antibodies raised against $CPS_{TSB}$ and $CPS_{CDM}$ recognize *B. anthracis* spores.

Hyperimmune serum raised against *Shewanella* spp. MR-4 as well as sera induced by conjugates reacted with *B. anthracis* spores as tested by fluorescent microscopy (FIG. 2A to 2D). As noted previously, in $CPS_{CDM}$ the hydroxybutyrate group is present in place of hydroxymethylbutyrate, which suggests that the methyl group is not important for the cross-reactivity. That corroborates the antigenicity results where the anti-spore sera recognized both CPS, non-methylated $CPS_{CDM}$ even with a higher titer (see Table 1). It is also possible that both methylated and non-methylated sugars are present on the spores.

Example 7

Recognition of *P. syringae* Bacteria by *Shewanella* Polysaccharide Antibodies

This example shows that serum antibodies raised against $CPS_{TSB}$ and $CPS_{CDM}$ recognize *P. syringae* bacteria.

*P. syringae* pv. *tabaci* 6605 was grown on King's medium for 24 h at 25° C. Hyperimmune serum against *Shewanella* sp. MR-4 reacted with *P. syringae* bacteria in immunodiffusion assay confirming that the common sugar present on either the capsule or the flagellum, respectively, is a cross-reactive moiety. FIG. 3A to 3B.

It will be apparent that the precise details of the methods or compositions described may be varied or modified without departing from the spirit of the disclosure. We claim all such modifications and variations that fall within the scope and spirit of the claims below.

We claim:

1. A method for stimulating an immune response against *B. anthracis* spores in a subject comprising administering to the subject an immune stimulating amount of a polysaccharide conjugate comprising -4)-β-D-Man-(1-4)-β-D-Glc-1-3-β-D-GlcNAc-(1-
                                              |
        4)-α-D-GlcA-(1-3)

conjugated to a carrier.

2. The method of claim 1, wherein the polysaccharide is covalently linked to a polymeric carrier.

3. The method of claim 1, wherein the carrier is a protein.

4. The method of claim 1, wherein the carrier is selected from bovine serum albumin, recombinant *B. anthracis* protective antigen, recombinant *P. aeruginosa* exotoxin A, tetanus toxoid, diphtheria toxoid, pertussis toxoid, *C. perfringens* toxoid, hepatitis B surface antigen, hepatitis B core antigen, keyhole limpet hemocyanin, or horseshoe crab hemocyanin.

* * * * *